(12) United States Patent
Renaville et al.

(10) Patent No.: US 6,492,142 B2
(45) Date of Patent: *Dec. 10, 2002

(54) PIT-1 GENE POLYMORPHISM AND TRAIT SELECTION IN ANIMALS

(75) Inventors: Robert Renaville, Gembloux (BE); Daniel Portetelle, Bruyere (BE)

(73) Assignee: Tomen Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/236,268

(22) Filed: Jan. 22, 1999

(65) Prior Publication Data

US 2001/0016315 A1 Aug. 23, 2001

Related U.S. Application Data

(63) Continuation of application No. PCT/EP97/03939, filed on Jul. 22, 1997.

(30) Foreign Application Priority Data

Jul. 22, 1996 (EP) .............................. 96401634

(51) Int. Cl.$^7$ ................................ C12P 19/34
(52) U.S. Cl. ................ 435/91.2; 435/6; 536/23.1; 536/23.5; 536/24.3; 536/24.32
(58) Field of Search .............. 536/23.5, 23.1, 536/24.32, 24.3; 435/6, 91.2

(56) References Cited

U.S. PATENT DOCUMENTS 5,614,364 A * 3/1997 Tuggle et al. .................. 435/6

FOREIGN PATENT DOCUMENTS

JP 6-90762 4/1994
WO WO 90/10714 9/1990

OTHER PUBLICATIONS

Mrode et al. Animal Production. 1994, 58:335–338.*
Klassen et al. Journal of Dairy Science. 1992, 756:2272–2282.*
T.-P. Yu et al., "Association of PIT1 Polymorphisms with Growth and Carcass Traits in Pigs", pp. 1282–1288, Journal of Animal Science, vol. 73, No. 5, May 1995.
J. Woollard et al. "Rapid Communication: HinfI Polymorphism at the Bovine PIT1 Locus", p. 3267, Journal of Animal Science, vol. 72, No. 12, Dec. 1994.
M. Bodner et al., "The Pituitary–Specific Transcription Factor GHF–1 Is a Homeobox–Containing Protein", pp. 505–518, Cell, vol. 55, Nov. 4, 1988.
T–P Yu et al., "Expression pattern, genomic cloning and RFLP analyses of the swine PIT–1 gene", pp. 229–233, Animal Genetics, vol. 25, No. 4, 1994.
J. Prosser, "Detecting single–base mutations", pp. 238–246, Trends In Biotechnology, vol. 11, Jun. 1993.
C.M. Mejdell et al., "Assoications of Bovine Lymphocyte Antigens with Milk and Meat Production Traits of Norwegian Cattle", pp. 3778–3784, Journal Dairy Science, vol. 76, No. 12, Dec. 1993.

* cited by examiner

*Primary Examiner*—W. Gary Jones
*Assistant Examiner*—Juliet Einsmann
(74) *Attorney, Agent, or Firm*—Young & Thompson

(57) ABSTRACT

The present invention relates to a genetic marker used to distinguish amongst animals a trait for milk producing capabilities or muscular beef producing capabilities, said genetic marker comprising a mutation in a fragment of a Pit-1 gene. After digestion with a restriction endonuclease, three allele patterns are observed, the fully digested pattern being indicative of a trait for muscularity in said animal, while the intermediate digested / nondigested pattern or the nondigested pattern being indicative of a milk producing trait in said animal. A process and kit using this genetic marker is also disclosed.

7 Claims, 4 Drawing Sheets

"MSCQPFTSTDTFIPLNSESSATLPLIMHPSAAECLPVSNHATNV
MSTATGLHYSVPFCHYGNQSSTYGVMAGSLTPCLYKFPDHTLSHGFPPMHQPLLSEDP
TAADFKQELRRKSKLVEEPIDMDSPEIRELEKFANEFKVRRIKLGYTQTNVGEALAAV
HGSEFSQTTICRFENLQLSFKNACKLKAILSKWLEEAEQVGALYNEKVGANERKRKRR
TTISIAAKDALERHFGEQNKPSSQEILRMAEELNLEKEVVRVWFCNRRQREKRVKTSL

```
1   gcaaatactg tgatttgaag ctaaccaaat aaactaattt ctatttggc tggagaagag 61  aaaggaatga aagtagaaac actcgctatt acacatagga gagcctatct gaattcgaga 121 tgctccttag aaatagtaaa taaactctga ttcaggcttg tcttcacccg ttttctctc 181 tgcttcggtt acaaaaccaa accctcacca cttctttctc caggtttagt tcttcagcca 241 tccgcaggat ctcctgagag gaaggcttat tctgttctcc aaagtgtctc tccagggcgt 301 ctttagcagc aatactgatt gttgttctcc gtttctattc ttttgtggga atgagttgcc 361 aaccttttac ttcgactgat acctttatac ctctgaattc tgagtcttct gcaactctgc 421 ctctgataat gcatcccagt gctgcggagt gcctaccggt ctccaaccac gccaccaacg 481 tgatgtccac agcaacagga cttcattatt ctgttccttt ctgtcattat ggaaaccagt 541 catcgaccta tggcgtgatg gcagggagct taacccctg tctttataag tttcctgacc 601 acacgttgag tcatggtttt cctcccatgc atcagcctct cctttcagag gaccccactg 661 ccgctgattt caagcaggag ctcaggcgga aaagcaaatt ggttgaagag ccaatagaca 721 tggattctcc agaaatccga gaacttgaaa agtttgccaa tgagtttaaa gtgagaagaa
```

FIGURE 2/1

```
 781 ttaagctagg atacacccag acaaatgttg gggaagctct ggcagctgtg catggctctg 841 aattcagtca aacaactatc tgccgatttg aaaacctgca gctcagcttc aaaaatgcat 901 gcaaactaaa agcaatatta tccaaatggc tggaggaagc cgagcaagta ggagctttat 961 acaatgagaa agttggtgca aatgaaagaa aaaggaaacg gagaacaaca atcagtattg 1021 ctgctaaaga cgcgctggag agacactttg gagaacagaa taagccttcc tctcaggaga 1081 tcctgcggat ggctgaagaa ctaaacctgg agaaagaagt ggtgagggtt tggttttgta Hinf-1
1141 accgaaggca gagagaaaaa cgggtgaaga caagcct|aaa tc|agagttta tttactattt
         ca gagagaaaaa cgggtgaaga caagcat a   (pit-1  AA)
         ca gagagaaaaa cgggtgaaga caagcat g   (pit-1  BB)

1201 ctaaggagca tctcgaatgc agataggctc tcctattgtg taatagcgat tctactttc 1261 attcctttct cttctcagcc aaaatagaaa ttagttattt ggttagcnnn aaaaatcaca 1321 tcagtaattt ttgncagaag tgtttctttt ctactttaaa aataaataca atttaaatta 1381 tgttgatgaa ntattctcag aaggannnnn tcantgtaca ntttaagcca aagactaata 1441 ggattaaaac aatgattctg t ccct t tcac tatatct t tc cctctatctc tcccnggaat
                        gac agggaaagtg atatagaaag ggagataga  (pit1-B)

PIT-1 GENE POLYMORPHISM AND TRAIT SELECTION IN ANIMALS

This application is a continuation of international application PCT/EP97/03939 filed Jul. 22, 1997, which in turn claims foreign priority to the European application 96401634.9, filed Jul. 22, 1996.

BACKGROUND OF THE INVENTION

Field of the Invention

The present invention relates to a genetic marker associated with different conformational traits. More specifically, the present invention describes a process wherein a polymorphism in a Pit-1 gene is used to determine traits in animals such as milk production and muscularity with ease.

Description of the Prior Art

Selection of a particular trait in a mammal is presently very expensive and very slow. Usually the selection process involves a genealogical evaluation of the mammals history over a long period of time. This evaluation is based on various traits of the mammal or animal such as birth weight, growth weight, build, muscle strength, firmness, marbling, color, and the like.

Most of the selection of a particular trait in an animal to date, involves visually characterizing the specific traits over a time frame or weighing the animal at particular times. The animals with the quality traits that are to be selected are then bred with similar animals such that the particular trait is hopefully dominant in the next generation or the generations to follow.

The present methods for trait selection in mammals are often tedious and open to judgment of an expert in the field, such as a breeder. However, there is never any real assurance that the choice being made will dominate over the forthcoming generations. For example, in order to select a cow that is a good milk producing animal, it takes between 36 to 48 months to make such choice and after the choice is made, it is often based on hypothesis and the breeder's judgment.

In view of the uncertainty, expense and time involved with the current methods of trait selection in animals, new methods are currently under development which methods utilize a more scientific process which will hopefully improve the selection process.

One such method is the study of candidate genes to determine whether specific genes are associated with conformational traits in mammals and therefore these genes can be used as molecular markers to select particular traits of interest. This method first requires identification of candidate genes or anonymous genetic markers associated with the traits of interest. The candidate gene approach can be successful, but first genes must be identified in the species of interest and correlated to the traits of interest.

The somatotropin system has several genes that may play a role in the control of particular traits in animals since this system is associated with growth, lactation, reproduction and immunity. The somatotropin system is quite complicated and involves at a hypothalamic level, somatocrinin and somatostatin; at a pituitary level, pituitary-specific transcription factor (Pit-1) which is responsible for growth hormone expression in mammals; at a hepatic level, growth hormone receptor and growth hormone plasmatic transport protein; and at a cellular level, growth hormone receptor, insulin-growth factor-1 and insulin growth factor transport protein.

Selection of genes from this somatotropin system that may influence particular traits in animals is quite complicated, since this system has many different functions in different parts of the animal, from the pituitary to the cellular level.

The present invention involves the selection of a gene, the pituitary-specific transcription factor (hereinafter referred to as Pit-1) that can act as a genetic marker to characterize specific traits in animals.

Pit-1 is a member of the POU family of homeo-domain transcription factors and plays an important role in developmental processes. The POU-domain was originally identified as a highly conserved region of 150 to 160 amino acids found in three mammalian transcription factors, Pit-1, Oct-1, Oct-2 and also in the product of nematode gene unc-86 (Herr et al., *Genes & Dev.* 2: 1513 (1988); Ruvkun and Finnery, *Cell* 64:475 (1991)).

Pit-1 is a pituitary-specific transcription factor that regulates growth hormone, activates prolactin and has a role in pituitary cell differentiation and proliferation (Steinfelder et al., *P.N.A.S.*, USA 88:3130 (1991). Mutations in the Pit-1 gene responsible for the dwarf phenotypes of the Snell and Jackson mice and lead to anterior pituitary hypoplasia (Li et al., Nature 347:528 (1992)). Moreover, it has been shown that the inhibition of Pit-1 synthesis leads to a decrease in prolactin and growth hormone (GH) expression and to a dramatic decrease in cell proliferation in GH and prolactin producing cell lines (McCormick et al., *Nature* 345:829 (1990)).

In human, different mutations in the Pit-1 gene have also been reported in patients with familial pituitary hypoplasia (Pfaffie et al., *Science* 257:1118 (1992)); and in patients with sporadic combined pituitary hormone deficiency (Radovick et al., *Science* 257:1115 (1992); Tatsumi et al., *Nature Genetics* 1: 56 (1992).

The cDNA sequence of bovine Pit-1 has been published by Bonder, M. et al, Cell 55 (3): 505–568 (1988)and is shown in FIG. 2 (SEQ ID NO:7).

The Association of Pit-1 polymorphisms with growth and carcass traits in pigs has been described by Yu et al., *J. Anim. Sci.* 73: 1282 (1995). Yu et al., supra described three Pit-1 polymorphisms in pigs based on two restriction fragment length polymorphisms (hereinafter referred to as RFLP) using a Pit-1 POU-domain cDNA probe and the restriction enzymes BamHI and MspI and a PCR/RFLP using RsaI.

Results from Yu et al.'s, supra, mixed-model analysis revealed that pigs with the MspI CC genotype were associated with heavier birth rate than the DD genotype pigs. Moreover, with the Pit-1 BamHI polymorphisms heavier birth weight was significantly associated with the BB genotype, although the authors cautioned against concluding such association since the BB genotype population was extremely small.

Although Woolard et al., *J. Anim. Sci.* 72:3267 1994) recognized a HinfI polymorphism at the bovine Pit-1 gene locus, these authors failed to link this mutation to the selection trait in animals. The conclusion drawn in Woolard, supra was that polymorphic fragments that were observed were consistent with autosomal Mendelian inheritance.

There is no disclosure in Yu et al. or Woolard et al of any association of the allele pattern AB with milk production, nor the allele pattern BB with muscularity in animals.

Therefore, the present invention overcomes the disadvantages of the current methods of trait selection in animals by providing a scientific basis for selection of traits by use of a genetic marker.

Moreover, the process described in the present invention can be used to characterize superior milk producing animals from animals having meat producing characteristics.

It has been surprisingly discovered that a polymorphism in the Pit-1 gene can be used to characterize traits such as milk production and muscularity in animals. Two alleles, A and B were distinguished for the Pit-1 gene responsible for the activation of prolactin and growth hormone gene expression. The AA pattern was less frequent than the AB or BB pattern. The significant superiority of the Pit-1 AB pattern or AA pattern over the BB pattern was observed for milk, protein and angularity. Likewise the BB genotype pattern was associated with animal muscularity.

This discovery permits the use of the mutation in the Pit-1 gene to be utilized as a genetic marker to identify certain traits in animals: Once these particular traits are identified, the animals can be sold at market with increased value due to their superior traits.

Accordingly, it is an object of the present invention to provide a genetic marker for trait selection in animals.

In another aspect, the present invention provides a process to characterize animals having superior milk production traits or muscularity traits.

In yet another aspect, the present invention provides genetically engineered animals that have superior milk production, angularity, fat, protein or muscularity traits. These and other objects are achieved by the present invention as evidenced by the summary of the invention, description of the preferred embodiments and the claims.

SUMMARY OF THE INVENTION

The present invention thus provides a genetic marker that can be used for trait selection in mammals.

Furthermore, the present invention provides a method to identify a polymorphism present in the Pit-1 gene which polymorphism can be utilized to select superior traits in animals for angularity, fat, muscularity, protein or milk production.

Accordingly, in one of the composition aspects, the present invention relates to a genetic marker used to distinguish amongst animals a trait for milk producing capabilities or meat producing capabilities said genetic marker comprising a mutation in a fragment of a Pit-1 gene, wherein three allele patterns are observed, the fully mutated pattern being indicative.

In the present application, the marker characteristic of milk producing capabilities is called AA for its homozygous state of the allele and the marker characteristic of meat producing capabilities is called BB for its homozygous state.

The sequences of alleles A and B differ only by one transition from the Adenosine in position 1178 of the sequence of FIG. 2 in Pit-1 AA to a guanine, in Pit-1 BB, as demonstrated by the inventors by experiments shown in Example B.

In a preferred embodiment for the present invention, the three allele patterns are distinguished after digestion with a restriction endonuclease, which cleaves the mutated Pit-1 gene fragment and not the non-mutated Pit-1 gene fragment, the fully digested pattern being indicative of a trait for muscularity in said animal, while the intermediate digested/non-digested pattern or the fully non-digested pattern being indicative of a milk producing trait in said animal.

In a more preferred embodiment of the present invention the restriction endonuclease utilized is HinfI.

In another preferred embodiment of the present invention, the three allele patterns are distinguished using probes which overlap the mutated region in said Pit-1 gene, one probe being specific for the mutated Pit-1 gene and another one being specific for the non-mutated Pit-1 gene.

In another aspect, the present invention relates to a process for detecting certain traits in an animal, said process comprising the steps of:

(1) isolating genomic DNA from an animal;
(2) optionally isolating a fragment from said genomic DNA comprising a fragment of a Pit-1 gene;
(3) detecting a mutation in the Pit-1 gene; and
(4) analyzing said mutation to determine a trait in said animal wherein upon analysis traits of muscularity and fat can be distinguished from milk producing traits in said animals.

In particular embodiment of the present invention, detection is accomplished by using restriction endonucleases.

In another particular embodiment of the present invention, detection is accomplished by using probes which overlap the mutated gene in said Pit-1 gene, more particularly the 1178 position.

In yet another aspect, the present invention relates to genetically engineered animals that have the characteristic traits described in the present invention.

BRIEF DESCRIPTION OF THE DRAWINGS

FIG. 2/1–2/2 is the sequence of bovine Pit-1 cDNA. The amino acid sequence set forth at the top of FIG. 2/1 corresponds to SEQ ID No: 6. The sequence ca gagagaaaaa cgggtgaaga caagcat a (pit-1 AA) corresponds to SEQ. ID No: 4. The sequence ca gagagaaaaa cgggtgaaga caagcat g (pit-1 BB) corresponds to SEQ. ID No: 5. The sequence gac aggggaaagtg atatagaaag ggagataga (pit1-B) corresponds to SEQ. ID No: 3.

Figure 1:
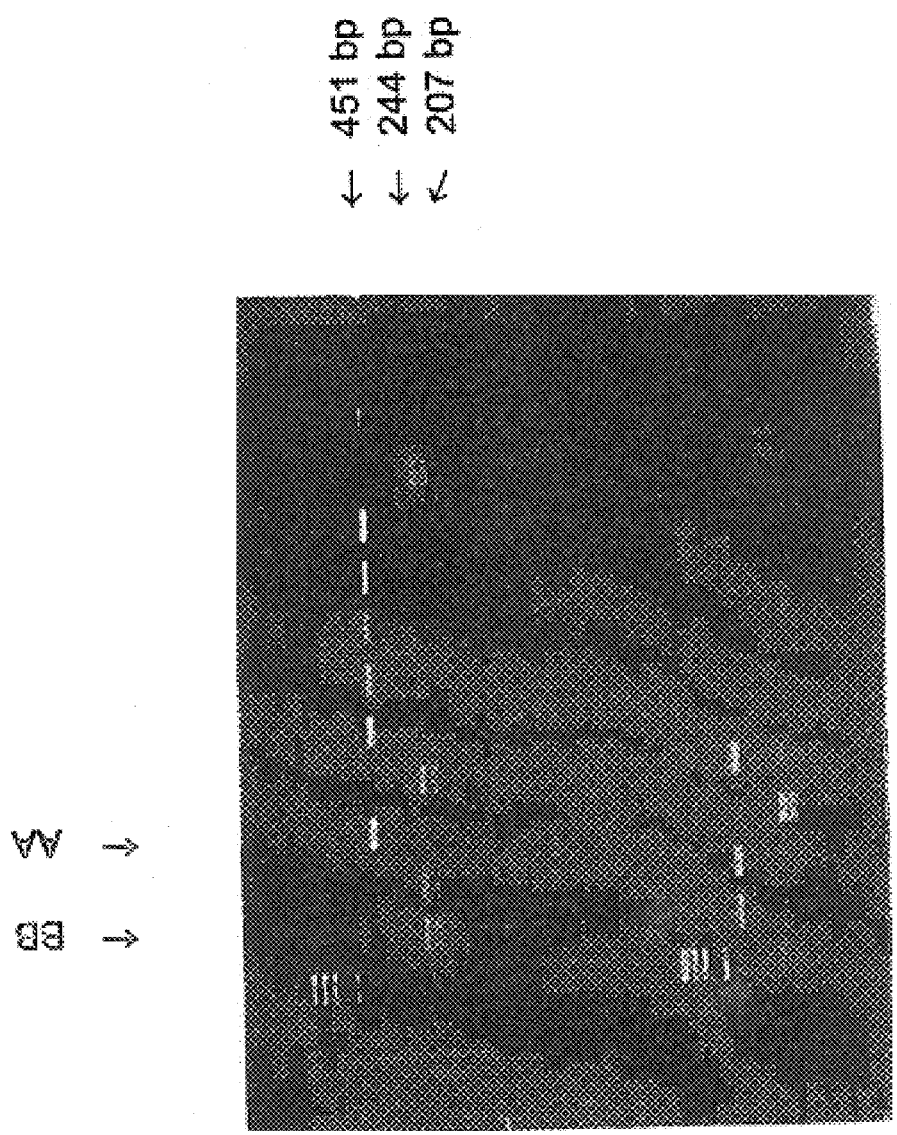
FIG. 1 is an electrophoretic gel illustrating the PCR/Restriction Fragment Length Polymorphism patterns using the restriction enzymes HinfI on the Pit-1 gene observed in Holstein-Friesian and Simmental Bulls. The sizes of digested fragments are on the left, and the patterns are at the top. Fragment length (in kilobases) was estimated relative to the DNA size markers φX174 DNA/HaeIII fragments.

lines 1-3-5 : Pit 1 AA and Pit 1 B,
lines 2-4-6 : Pit 1 BB and Pit 1 B.

DETAILED DESCRIPTION OF THE PREFERRED EMBODIMENTS OF THE INVENTION

As used herein, the "animal" encompasses all mammals, avians, and fish including but not limited to, cows, bulls, goats, pigs, sheep, chickens and the like. In view of the high degree of conservation of the Pit-1 gene among species (>95%) the invention is easily transposable from one specie to another. Also, the instant invention can be used in human beings to determine traits such as capacity to metabolize growth hormone.

The term "polymorphism" refers to the simultaneous occurrence in the population of genomes showing allelic variations as seen either in alleles producing different phenotypes or in changes in DNA affecting the restriction pattern.

As used herein the term "trait" encompasses any characteristic, especially one that distinguishes one animal from another.

The term "angularity", as used herein means an objective criteria used to identify specific traits of an animal in relation to specific measurements which can be taken on the animal's body. The measurements are taken on the animal with respect to certain morphological characteristics.

For example, to determine the angularity for a milk production trait, the pelvic bones and muscles surrounding the pelvic bones of an animal are measured to determine whether they are projecting or not. A scale can then be established. When the bones are very projecting, there are very little rounded muscles and thus the animals are milk producing. To the contrary, when the bones are not protruding and there are a lot of rounded muscle present on the animal, the animal would not be considered a good milk produce, but rather a beef producer.

As used herein, the term "muscularity" encompasses animals that are better meat producers that can be slaughtered for their meat than milk producers.

More specifically, the present invention relates to the use of a Pit-1 gene polymorphism as a potential marker for genetic variations in animals. Pit-1 codes for a factor of transcription in a cell and any mutation of this gene can alter by diminution or augmentation the capacity of transcription thus resulting in polymorphisms which effect the outcome of different traits in an animal.

The Pit-1 gene was previously identified in a 13-kb bovine genomic library by Woolard et al., supra. A 13-kb clone was isolated from this library by using a bovine Pit-1 cDNA, which is labeled, as a probe of:

```
5'-AAACCATCATCTCCCTTCTT-3'    (SEQ. ID. NO: 1)

5'-AATGTACAATGTGCCTTCTGAG-3'  (SEQ. ID. NO:2)
```

Characterization of XhoI, HinfI and EcoRI subclones of this 13-kb insert by restriction enzyme digestion and sequencing identified this clone as a bovine Pit-1 genomic fragment.

Similarly methods as taught by Woolard et al, supra can be used to identify the Pit-1 gene in different genomic libraries other than bovine. This will permit the identification of specific sequences within the Pit-1 genomic fragment that can be used to amplify this sequence from different animals as described below.

The first step in identifying a mutation in the Pit-1 gene in an animal is to obtain a sample from the animal such as, but not limited to semen, blood, cells, biopsy tissues, feces and the like. Genomic DNA can then be extracted for the specimens obtained using methods known in the art as described by Sambrook et al., *Molecular Cloning, A Laboratory Manual*, second edition 1989.

However, it is preferable to extract the genomic DNA using the procedure described in Walsh, *Biotechniques*, 10:506 (1991) for semen or the procedure for blood as described by Lewin and Stewart-Haynes *Biotechniques*, 13:522.

After extracting the genomic DNA there are several known methods in the art to detect the mutation in the Pit-1 gene. Any detection method can be utilized to detect the mutation. Examples of these methods include, but are not limited to RFLP, SSCP, DGGE, CFLP and single base mutations as described by Prosser, *Trends Biotech* 11:238–246 (1993) and Sambrook et al..supra. These methods will be discussed in greater detail below.

For example, in the RFLP (restriction fragment length polymorphism) method, PCR primers are used to amplify by standard procedures a fragment that includes the Pit-1 gene. Any PCR primers can be utilized that would permit the amplification of the Pit-1 sequence and the method in isolating the particular clone which would identify such primers.

In a preferred embodiment of the invention, the PCR primers can be designed from intron V and exon 6 of a fragment containing the polymorphism of the Pit-1 gene, such as the 451-bp fragment described by Woolard et al.,supra. In a more preferred embodiment of the present invention, the PCR primers are as follows:

```
5'-AAACCATCATCTCCCTTCTT-3'    (SEQ. ID. NO: 1)

5'-AATGTACAATGTGCCTTCTGAG-3'  (SEQ. ID. NO:2)
```

Amplification of the Pit-1 fragment can be performed using standard PCR procedures, as described in Sambrook et al.,supra. It is preferable, however, to amplify the genomic DNA in a 50 $\mu l$ reaction volumes containing 2 mM $MgCl_2$.

In a preferred embodiment of the invention, the following conditions for the PCR reaction can be employed: between 88° C. to 98° C. for 10 to 15 i minutes; and between 90° C. to 100° C. for about 1 minute, followed by between 25 to 50 cycles at between 90° C. to 100° C. for 20 to 40 seconds; 40° C. to 60° C. for 1 to 5 minutes; and 68° C. to 80° C. for about 1 to 5 minutes. The last step may encompass a cycle at between 68° C. to 80° C. for 8 to 12 minutes.

After amplification the particular mutation in Pit-1 is then cut using various restriction enzymes or endonucleases known in the art. These restriction enzymes include, but are not limited to BamHI, EcoRI, SmaI, HinfI and the like. See, for example those enzymes described in Sambrook et al., supra. It is of particular interest to use a restriction endonuclease which cleaves the mutated allele of the Pit-1 gene and does not cleave the non-mutated allele of the Pit-1 gene. In a preferred embodiment of the present invention with the respect to the identification of milk production, fat, protein and muscularity traits in animals, HinfI is utilized.

After digestion, the sample is then electrophoresed on agarose gels and identified with a stain such as, for example ethidium bromide, however any stain can be used that identifies the fragments SCCP(single stranded conformation polymorphism) is also a method known in the art that can identify a mutation or mutations in the isolated genomic Pit-1 fragment. This method is based on PCR amplification, using similar primers as those described above. The amplified fragment is then labeled with a label such as $^{32}P$ or with any other appropriate radioactive label. The radiolabeled fragment is then denatured, for example by heating and then subjected to quick cooling. After cooling, the fragment is then electrophoresed using non-denatured technique and then audioradiographed.

DGGE (denaturing gradient gel electrophoresis) is yet another method to detect the Pit-1 mutation. In this process, the fragment is amplified by PCR using appropriate primers, such as those described above and subjected to a denaturing gradient. The sample is further electrophoresed and the mutation is detected.

Yet another method that can be used to detect the mutation is CFLP (cleavage fragment length polymorphism). This method can detect mutations of a sole base in the DNA sequence between two molecules of wild-type DNA and of a mutant type of DNA This method is now marketed by Boehringer Mannheim and can be purchased in the form of a kit.

Another method that can be used to detect the mutation in the Pit-1 gene utilizes primers that overlap the mutated region of the Pit-1 gene.

More preferably, two separate amplification reactions are performed on the extracted genomic DNA sample using two sets of primers, one set containing a primer which overlaps and is specific for the mutated Pit-1 gene, another set containing a primer which overlaps and is specific for the non-mutated Pit-1 gene. Even more preferably, the primers used are labeled so it that the amplification product can be easily visualized. According to this method, when the tested genomic DNA contains a homozygous mutated Pit-1 gene (two mutated alleles), only the amplification reaction using the probe specific for the mutated region will produce a signal (i.e., an amplification product). When the tested genomic DNA is heterozygous (one mutated allele and one non-mutated allele) the two amplification reactions will produce a signal (an amplification product). Similarly, when the tested genomic DNA contains a homozygous non-mutated Pit-1 gene, only the amplification reaction using the probe specific for the non-mutated region will produce a signal. Therefore, in one single amplification step, the allele pattern of the tested DNA becomes apparent.

In a second embodiment, the use of technique described in WO 97/06276 is particularly adapted to detect in a single step the homozygous or heterozygous state of the marker.

In these methods, there is no need to further cut the amplified product in order to distinguish among the various patterns. Furthermore, there is no need to amplify a specific Pit-1 gene fragment prior to the detection step. Finally, depending on the nature of the label used, the visualization can be very easy. For instance, when the probes are radiolabelled visualization is obtained by electrophoresis. More interestingly, when the probes are labelled with stains, immediate visualization is obtained.

In the first embodiment, the test can be carried out in very simple devices, such as plates. Samples of the genomic DNA are introduced into 2 wells, one with the labeled set of probes containing one probe which overlaps the Pit-1 gene mutation and is specific for the mutated Pit-1 gene, one with the set of probes containing one probe which overlaps the Pit-1 gene mutation and is specific for the non-mutated Pit-1 gene.

After amplification, the labelling appears directly in the plates and can be analyzed by automated devices.

In this amplification method, the second primer used in each of the set of probes is selected in such a way as to enable amplification of a product containing from 200 to 400 bp. More preferably 320–370 bp. Such second primers can be for instance selected from the following primers:

gac agggaaagtg atatagaaag ggagataga (Pit-1 B) (SEQ ID No:3)

The length of each of the primers is preferably comprised between 20 and 40 bases, more preferably between 25 and 35.

The selection of the appropriate probes for this strategy has been made possible by the identification, by the inventors, of a mutation in the Pit-1 gene that is responsible for the observed polymorphism. More specifically, this mutation occurs in the Pit-1 coding region, at nucleotide 1178, where an Adenine is substituted in the mutated gene by a guanine. This mutation is shown in FIG. 2.

The position of the probe which overlap the mutated region (the mutation) can vary.

More preferably, in the first embodiment, the two couples of primers are:

ca gagagaaaaa cgggtgaaga caagcat a (Pit-1 AA) (SEQ ID No:4)

gac agggaaagtg atatagaaag ggagataga (Pit-1 B) for the AA genotype, characteristic of milk producing capabilities, and ca gagagaaaaa cgggtgaaga caagcat g (Pit-1 BB) (SEQ ID No:5)

gac agggaaagtg atatagaaag ggagataga (Pit-1 B) (SEQ ID No:3) for the BB genotype, characteristic of meat producing capabilities.

In the second embodiment, when the method of WO 97/06276 is used, two couples of primers leading to the production of amplified fragments of different sizes are:

ca gagagaaaaa cgggtgaaga caagcat a (Pit-1 AA) (SEQ ID No:4)

gac agggaaagtg atatagaaag ggagataga (Pit-1 B) (SEQ ID No:3) for the AA genotype, characteristic of milk producing capabilities, and ca gagagaaaaa cgggtgaaga caagcat g (Pit-1 BB) (SEQ ID No:5) and a second primer Pit-1 C' chosen in such a way that the amplification is at least 10 bp shorter or longer than those obtained with Pit-1 AA and Pit-1 B for the BB genotype, characteristic of meat producing capabilities.

Although many detection methods for mutations are available, the present invention is not limited to the methods discussed above and encompasses all methods for detecting a mutation.

The alleles and allelic patterns are then identified and statistical analysis is then performed to determine the specific traits evidenced by the identification of the alleles. More specifically, any statistical program that can identify daughter yield variations (DYD) and deregressed proofs (DRP) can be utilized. It is preferable to perform the statistical analysis using the MIXED procedure of SAS (User's Guide:Statistics, Version 6, 4th ed. SAS Inst., Inc. Cary, N.C. (1990), Technical Report P 229 SAS Inst., Inc., Cary, N.C. (1992). The statistical analysis used in the present invention is discussed in detail in the examples below.

Also encompassed by the present invention is a kit containing extraction materials for genomic DNA, the PCR primers having SEQ ID NOS. 1 and 2 (illustrated above), the materials necessary to visualize the mutation such as electrophoretic gels and the like. The content of the kit may vary depending upon the detection methods utilized, which are discussed in detail above.

Also encompassed by the present invention are primers that overlap the mutation in the Pit-1 gene.

More specifically, the invention also relates to a primer comprising from 20 to 40 bases, which is complementary to a region of the Pit-1 gene having a mutation.

The invention also embraces sets of primers which allow the amplification of a region of 200 to 400 bases in the Pit-1 gene, wherein said region contains a mutation.

The following primers are encompassed in the present invention:

ca gagagaaaaa cgggtgaaga caagcat a (Pit-1 AA) (SEQ ID No:4)

ca gagagaaaaa cgggtgaaga caagcat g (Pit-1 BB) (SEQ ID No:5)

gac agggaaagtg atatagaaag ggagataga (Pit-1 B) (SEQ ID No:3)

In order to further illustrate the present invention and advantages thereof, the following specific examples are given, it being understood that the same are intended only as illustrative and in nowise limitative.

EXAMPLE A

1. DNA EXTRACTION AND PCR

Genomic DNA of 89 commercially available registered Italian Holstein-Friesian bulls was extracted from semen as described by Lucy et al., *Domest. Anim. Endocrinol.* 10:325 (1993).

The RFLP at the Pit-1 gene using HinfI restriction enzyme was revealed by PCR analysis adapted from Woolard et al., supra.

The PCR primers were designed from intron V and exon 6 The sequences of the primers used were 5'-AAACCATCATCTCCCTTCTT-3' (SEQ ID NO:1) and 5'-AATGTACAATGTGCCTTCTGAG-3' (SEQ ID NO:2). These primers were used to amplify by standard procedures a 451-bp fragment form the genomic DNA in 50-μL reaction volumes containing 2 mM $MgCl_2$. Conditions were 94.5° C., 10 min., and 94° C., 1 min., followed by 35 cycles of 95° C., 30 s, 56° C., 1 min., and 72° C., 2 min. The last step was 72° C. for 10 min. PCR products were digested with HinfI and electrophoresed on 2% agarose gels with 1 μg/mL ethidium bromide (FIG. 1).

Daughter yield deviations (DYD) computed in March 1996, were obtained from the Holstein-Friesian bulls from the Italian Holstein-Friesian Breeder Association ANAFI (Associazione Nazionale Allevatori Frison Italiana, Cremona, Italy). DYD values are not computed for fat and protein percentage as those traits are only evaluated indirectly out of solutions for yield traits and mean population values for those traits. Therefore DYD values were computed using the same approach as for the computation of genetic values for percentage traits.

Similar DYD were also not available for type traits, therefore genetic values were transformed to deregressed proofs (DRP) (Banos et al., Interbull Annual Meeting, Aarhus, Denmark, Bulletin No. 8, 1993, Sigbjorn et al., *J. Dairy Sci*, 78:2047 (1995)) that can then be considered approximate DYD.

Means and standard deviations of DYD for milk production traits and or DRP for conformation traits of the bulls sample are presented in Table I. Effective number of daughters, which is a measure of the number of daughters adjusted for their distribution inside herds was available for yield traits, but not for type traits. It was therefore approximated using the following formula: effective number=real number×square root of ratio between number of herds and number of daughters.

TABLE I

TABLE 1. Mean daughter yield deviations for milk traits and deregressed proofs for conformation traits of 89 Holstein-Friesian bulls.

| Trait | $\overline{X}$ | SD | Minimum | Maximum |
|---|---|---|---|---|
| Milk traits | | | | |
| Milk, kg | +317 | 221 | −231 | +899 |
| Fat, kg | +10.8 | 8.2 | −14 | +28 |
| Protein, kg | +11.6 | 7.2 | −7 | +32 |
| Fat, %[1] | −0.003 | 0.091 | −0.17 | +0.23 |
| Protein, %[1] | +0.021 | 0.045 | −0.11 | +0.12 |
| Effective daughters[2] | 490 | 1443 | 69 | 10298 |

TABLE I-continued

TABLE 1. Mean daughter yield deviations for milk traits and deregressed proofs for conformation traits of 89 Holstein-Friesian bulls.

| Trait | $\overline{X}$ | SD | Minimum | Maximum |
|---|---|---|---|---|
| Conformation traits[3] | | | | |
| Final score | +0.147 | 0.438 | −0.75 | +1.19 |
| Stature | +0.210 | 1.536 | −3.76 | +4.56 |
| Strength | +0.218 | 1.662 | −3.68 | +3.46 |
| Body depth | +0.340 | 1.599 | −3.42 | +3.64 |
| Angularity | +0.681 | 1.215 | −3.44 | +3.42 |
| Rump angle | −0.111 | 1.807 | −4.44 | +4.10 |
| Rump width | +0.007 | 1.591 | −3.28 | +4.34 |
| Rear legs | +0.203 | 2.266 | −5.66 | +5.66 |
| Feet | +0.053 | 1.746 | −5.26 | +3.84 |
| Fore udder | +0.038 | 2.207 | −5.44 | +5.46 |
| Heigth rear udder | +0.458 | 1.856 | −3.64 | +4.44 |
| Width rear udder | +0.864 | 1.474 | −2.80 | +4.18 |
| Udder support | +0.514 | 2.453 | −10.72 | +7.12 |
| Udder depth | −0.282 | 1.702 | −5.78 | +3.74 |
| Teat placement | +0.479 | 1.633 | −4.12 | +3.82 |
| Teat length | +0.416 | 2.112 | −4.60 | +6.74 |
| Effective daughters[4] | 195 | 471 | 18 | 3199 |

[1]Percentage fat and protein daughter yield deviations computed from yields.
[2]Number of effective daughters for yield reported by ANAFI.
[3]Deregressed proofs for final score reported on original scale, for linear scores on relative scale
[4]Approximate number of effective daughters obtained from numbers of daughters and herds.

2. STATISTICAL ANALYSIS

Statistical analysis was performed using the MIXED procedure of SAS supra. The mixed model used was $$y=Xb+Zu+e$$

Where y=vector of DYD or DRP of bulls; b=vector of fixed effects associated with Pit-1 pattern, u=vector of random additive polygenic effect of bulls, and e=vector of random residual effects. This model was solved using the following mixed model equations:

$$\begin{bmatrix} X'R^{-1}X & X'R^{-1}Z \\ Z'R^{-1}X & Z'R^{-1}Z+A^{-1}\left(\frac{4-h^2}{h^2\hat{\sigma}_e^2}\right) \end{bmatrix} \begin{bmatrix} \hat{b} \\ \hat{u} \end{bmatrix} = \begin{bmatrix} X'R^{-1}y \\ Z'R^{-1}y \end{bmatrix} \Leftrightarrow \begin{bmatrix} C_{bb} & C_{bu} \\ C_{ub} & C_{uu} \end{bmatrix} \begin{bmatrix} \hat{b} \\ \hat{u} \end{bmatrix}$$

$$= \begin{bmatrix} X'R^{-1}y \\ Z'R^{-1}y \end{bmatrix}$$

where A is the additive relationship matrix between the 89 bulls constructed using all known relationships (1842 known ancestors), $R^{-1}=D/\hat{\sigma}_e^2$ where D is assumed to be a diagonal matrix with the number of effective daughters for every bull on its diagonal. This matrix is then divided by the estimate of the residual variance $\hat{\sigma}_e^2$. This is a REML estimated (Patterson and Thompson,*Biometrika* 58:545

91971), here identical to non-interactive minimum variance quadratic unbiased estimation (Rao, *J. Mult. Anal.* 1:445 (1971), as convergence occurs after 1 round. The estimate found has the property of being the quadratic forms minimizing the sampling variance. Two assumption were made, no residual covariances between DYD or DRP and heritabilities ($h^2$) of DYD or DRP equal to heratibilities use for genetic evaluations with the exception of percentage of fat and protein where 0.50 was assumed to be the heritability (Table 2). This method tends to overestimate additive heritability as variance due to sires is not reduce for the presence of the Pit-1 pattern in the model, but this overestimation should be not very important.

TABLE II

TABLE 2. Assumed heritabilities and milk traits and conformation traits of Italian Holsteins.

| Trait | Heritability |
|---|---|
| Milk traits | |
| Milk, kg | 0.25 |
| Fat, kg | 0.25 |
| Protein, kg | 0.25 |
| Fat, %[1] | 0.50 |
| Protein, %[1] | 0.50 |
| Conformation traits | |
| Final score | 0.15 |
| Stature | 0.38 |
| Strength | 0.29 |
| Body depth | 0.31 |
| Angularity | 0.31 |
| Rump angle | 0.25 |
| Rump width | 0.29 |
| Rear legs | 0.16 |
| Feet | 0.18 |
| Fore udder | 0.15 |
| Height rear udder | 0.20 |
| Width rear udder | 0.24 |
| Udder support | 0.15 |
| Udder depth | 0.29 |
| Teat placement | 0.22 |
| Teat length | 0.22 |

[1]Percentage fat and protein daughter yield deviations computed from yields, therefore assumed heritability is not the heritability used for breeding value estimation.

Linear contrasts were constructed as differences between pattern solutions. Testing of contrasts was done using the following statistic:

$$F = b'l - l'C^{bb}l)^{-1}l'b$$

where l'b represents differences between pattern solutions, l being the linear contrast vector, $C^{bb}$ an estimate of the block of the generalized inverse of the coefficient matrix associated with pattern effects and $(l'C^{bb}l)^{-1}$ is the inverse of the squared standard error of the linear contrast. The numerator degree of freedom was approximated using rank (l)=1. The denominator was put to n−rank(X)=86 where n is the number of observations.

It is not certain that the presence of a given pattern has only one major effect. Therefore the following strategy based of Weller et al., *J. Dairy Sci.* 73: 2525 (1990) was used to test this hypothesis.

1. Traits showing single-trait significant contrasts between patterns were grouped, eventual related traits were also included.

2. Weighted correlation V and covariance P matrixes among these traits were obtained.

3. A canonical transformation was defined as V=QEQ', where E is a diagonal matrix of eigenvalues, and Q a matrix of eigenvectors.

4. The transformation matrix T was defined as $Q^{-1}S$ where S is a diagonal matrix of the inverse standard-deviations of the original traits, therefore TPT'=E.

5. The transformation matrix was used to transform the related traits to unrelated canonical traits.

6. Approximate heritabilities and weights for the canonical traits were obtained as weighted averages of the values for the initial traits, weighting coefficients were the squared values of $Q^{-1}$.

7. Canonical traits were analyzed using the methods described above for initial traits. Canonical traits showing only low relative eigenvalues explain little of the observed variance.

8. Multiple-trait linear contrasts for original effects can be estimated using back transformation of significant canonical contrasts.

9. The results for these new traits are then useful to determine if only one effect of the Pit-1 pattern can be observed, or if there are more than one significant effects. Backtransformed contrasts reflect the significant differences between original traits based on a given effect of Pit-1 on the canonical trait.

3. RESULTS

PCR/RFLP

The PCR product was 451 bp in length. Digestion of the PCR product with HinfI revealed two alleles: the A allele not digested with HinfI and yielding a 451 bp fragment and the B allele cut at one restriction site and generating two fragments of 244 and 207 bp in length as described by Woollard et al., supra (FIG. 1).

Relationship of PCR/RFLP to Milk production

The frequencies of the three pattern AA, AB, and BB were 2.2%, 31.5% and 66.3%. The frequencies of the A and B alleles were estimated by a maximum likelihood approach with 18.8% for A and 81.2% for B.

Table 3 shows the linear contrasts and standard errors between the three Pit-1 pattern. Therefore the highly significant contrasts (P<0.01) observed for rear legs seem to be more due to the fact that the typed AA animals are extreme on this trait than to a real biological reason. Highly significant contrasts between AB and BB patterns were found for milk and protein yield (P<0.01). Significant contrasts were observed for fat percentage and angularity (P<0.05). The AB pattern or AA pattern was superior for milk, protein yield and angularity and inferior for fat percentage. These results can be interpreted as resulting from a single positive action of the heterozygote AB or AA on milk yield, thereby influencing protein yield positively and not fat yield which gives the observed negative influence on fat percentage. The influence of Pit-1 on angularity is in this context not very surprising as this linear trait is considered being strongly related to milk yield.

TABLE III

TABLE 3. Linear contrasts (C) and standard errors (SE) between the three Pit-1 patterns observed on 89 Holstein-Friesian bulls.

| | Contrast | | | | | |
|---|---|---|---|---|---|---|
| | AA-AB[1] | | AA-BB[1] | | AB-BB | |
| Trait | C | SE | C | SE | C | SE |
| Milk traits | | | | | | |
| Milk, kg | −152 | 156 | −21 | 150 | 131** | 49 |
| Fat, kg | 5.0 | 5.7 | 5.4 | 5.7 | 0.4 | 1.8 |
| Protein, kg | −4.2 | 4.9 | 0.8 | 4.5 | 4.9** | 1.5 |
| Fat, %[2] | 0.114 | 0.062 | 0.067 | 0.062 | −0.047* | 0.019 |
| Protein, %[2] | 0.005 | 0.034 | 0.015 | 0.031 | 0.010 | 0.010 |
| Conformation traits[3] | | | | | | |
| Final score | −0.376 | 0.299 | −0.253 | 0.298 | 0.123 | 0.092 |
| Stature | −0.745 | 1.043 | −0.501 | 1.044 | 0.244 | 0.329 |
| Strength | 0.915 | 1.143 | 1.012 | 1.138 | 0.097 | 0.367 |
| Body depth | 0.108 | 1.076 | 0.562 | 1.061 | 0.454 | 0.332 |
| Angularity | −0.478 | 0.809 | 0.072 | 0.716 | 0.550 | 0.252* |
| Rump angle | −0.211 | 1.219 | −0.514 | 1.286 | −0.303 | 0.398 |
| Rump width | 0.019 | 0.608 | 0.147 | 1.039 | 0.128 | 0.330 |
| Rear legs | −4.404**[1] | 1.548 | −4.784**[1] | 1.542 | −0.380 | 0.479 |
| Feet | 1.588 | 1.264 | 1.731 | 1.259 | 0.142 | 0.395 |
| Fore udder | −0.653 | 1.540 | −1.256 | 1.546 | 0.603 | 0.478 |
| Heigth rear udder | −0.974 | 1.290 | −0.998 | 1.288 | −0.024 | 0.750 |
| Width rear udder | −0.378 | 1.047 | 0.072 | 2.273 | 0.449 | 0.324 |
| Udder support | −1.798 | 1.707 | −1.157 | 1.706 | 0.641 | 0.525 |
| Udder depth | −1.447 | 1.245 | −1.673 | 1.240 | −0.226 | 0.388 |
| Teat placement | −1.385 | 1.158 | −1.548 | 1.154 | −0.163 | 0.356 |
| Teat length | 0.041 | 1.297 | 0.312 | 1.396 | 0.271 | 0.446 |

[1]Only 2.2% of the animal were AA, therefore all results comparing this pattern are preliminary
[2]Percentage fat and protein daughter yield deviations computed from yields.
[3]Deregressed proofs for final score reported on original scale, for linear scores on relative scale.
*P < 0.05
**P < 0.01

In order to test the hypothesis of a single action we performed a canonical transformation of milk, fat and protein yields. Yields were analyzed as percentage DYD were obtained as functions of yields; therefore this results in no new information. Angularity was added. The phenotypic correlation matrix was computed. Observations were weighted using the number of effective daughters. Since these numbers were different for yield and type traits approximate weights were obtained as weighted means of numbers of effective daughters. Table 4 gives the correlations. Correlations among yield traits showed the expected values with higher correlations between milk and protein than between fat and one of the other traits. Angularity showed correlations between 0.42 and 0.51 with yields traits.

TABLE 4

Correlations among daughter yield deviations for the milk traits and angularity

| | Trait | | | |
|---|---|---|---|---|
| Trait | Milk yield | Fat yield | Protein yield | Angularity |
| Milk yield | 1.00 | 0.72 | 0.90 | 0.42 |
| Fat yield | | 1.00 | 0.76 | 0.51 |
| Protein yield | | | 1.00 | 0.48 |
| Angularity | | | | 1.00 |

Results from the canonical decomposition of the correlation matrix are in table V. The first and the second canonical trait explain 90% of the total variance. Especially the last canonical trait was not very informative. Table 5 gives also the eigenvectors and the relative importance of the different traits in each eigenvector. The first canonical trait is a combination of all four traits with relative influences between 15% for angularity and 30% for protein. The second canonical trait however is more specifically linked to angularity with a relative importance of 81% in this trait. The third is associated with fat and less with milk, the fourth only with milk and protein.

TABLE 5

Standardized eigenvectors and eigenvalues of the four canonical traits (between bracketts relative importance of eigenvalues in total variance and of values in eigenvectors in canonical traits).

| Canonical Trait | Eigenvalue | Eigenvector | | | |
|---|---|---|---|---|---|
| | | Milk yield | Fat yield | Protein yield | Angularity |
| 1 | 2.94 (73%) | 0.532 (28%) | 0.515 (27%) | 0.548 (30%) | 0.389 (15%) |
| 2 | 0.67 (17%) | 0.349 (12%) | 0.047 (<1%) | 0.257 (7%) | −0.900 (81%) |
| 3 | 0.30 (8%) | 0.396 (16%) | −0.853 73%) | 0.283 (8%) | 0.189 (4%) |
| 4 | 0.09 (2%) | 0.662 (44%) | 0.072 (<1%) | −0.744 (55%) | 0.048 (<1%) |

Table 6 shows the linear contrasts and standard-errors observed for the four canonical traits. Against the expectations the first and the second canonical traits were found very highly significant (P<0.001) and the fourth was slightly significant (P<0.05) for the contrasts between the AB and BB pattern. This result showed that Pit-1 could have more than one action. The first canonical trait is more specifically linked to angularity. The last trait reflected the equilibrium between milk and protein yields. In order to make these contrasts more understandable, table 7 gives the values of the contrasts and the standard errors expressed on the original scales. We observed that the backtransformed contrasts were very important for milk, fat and protein for the first canonical contrast. All were also positive with AB animals superior to BB animals. For the second canonical trait the AB were inferior for milk, fat and protein and superior for angularity. This indicates again that the influence of Pit-1 on angularity seems to be important, first through the link between yields and angularity, but also directly on angularity with a slightly negative influence on yields. Canonical trait three did not show significant contrasts and canonical trait four, despite being significant, explained only very little of the total variance. After grouping all the significant canonical traits together, we observed higher grouped contrasts as in the single-trait situation. This was especially clear for fat yield and angularity, but also for milk and protein. The reason seems to be that the multiple-trait contrasts include information from the correlated traits, especially for fat and angularity this could explain the differences. Standard errors of contrasts did not increase in an important way, they were even reduced for milk and fat yields.

TABLE 6

Linear contrasts (C) and standard errors (SE) between the three Pit-1 patterns for the four canonical traits observed on 89 Holstein-Friesian bulls.

| Canonical trait | Contrast | | | | | |
|---|---|---|---|---|---|---|
| | AA-AB[1] | | AA-BB[1] | | AB-BB | |
| | C | SE | C | SE | C | SE |
| 1 | −0.093 | 0.098 | 0.023 | 0.093 | 0.116*** | 0.017 |
| 2 | 0.003 | 0.102 | −0.032 | 0.052 | −0.035*** | 0.009 |
| 3 | −0.021 | 0.038 | −0.016 | 0.037 | 0.005 | 0.007 |
| 4[2] | 0.005 | 0.021 | −0.004 | 0.021 | −0.009* | 0.004 |

[1]Only 2.2% of the animal were AA, therefore all results comparing this pattern are preliminary.
[2]Eigenvalue associated with canonical trait 4 was very low, therefore the results should be interpreted as non-significant.
*P < 0.05
***P < 0.001

TABLE 7

Linear contrast (C) and standard error of contrast (SE) between AB and BB obtained by backtransformation on 89 Holstein-Friesian bulls.

| Trait | Canonical trait | | | | | | | | | |
|---|---|---|---|---|---|---|---|---|---|---|
| | 1*** | | 2*** | | 3 | | 4* | | All significant[1] | |
| | C | SE | C | SE | C | SE | C | SE | C | SE |
| Milk yield | 289 | 44 | −57 | 15 | 9 | 13 | −27 | 11 | 205 | 48 |
| Fat yield | 12.6 | 1.9 | −0.3 | 0.1 | −0.9 | 1.2 | −0.1 | 0.1 | 12.1 | 1.9 |
| Protein yield | 8.6 | 1.3 | −1.2 | 0.3 | 0.2 | 0.3 | 0.9 | 0.4 | 8.3 | 1.4 |
| Angularity | 1.126 | 0.169 | 0.782 | 0.211 | 0.223 | 0.032 | −0.010 | 0.004 | 1.897 | 0.271 |

[1]Combined linear contrast using the three significant canonical traits
*P < 0.05
***P < 0.001

EXAMPLE B

Sequencing of the Pit-1 gene and characterization of a mutation.

This method generates separate populations of radiolabeled oligonucleotides that begin from a fixed point and terminate randomly at a fixed residue or combination of residues. Because every base in the DNA has an equal chance of being a variable terminus, each population consists of a mixture of oligonucleotides whose lengths are determined by the location of a particular base along the length of the original DNA. These populations of oligonucleotides are then resolved by electrophoresis under conditions that can discrimate between individual DNAs that differ in length by as little as one nucleotide. When the populations are loaded into adjacent lanes of a sequencing gel, the order of nucleotides along the DNA can be read directly from an autoradiographic image of the gel. Reference: Sanger, F., S. Nicklen, and A. R. Coulson. 1977, DNA sequencing with chain-terminating inhibitors, *Proc. Natl. Acad. Sci.* 74:5463.

EXAMPLE C

Detection experiments using the primers.

1) Ligase Chain Reaction.

Ligase chain reaction (LCR), employing just oligonucleotide probes and DNA ligase, is capable of detecting approximately 1000 copies of a specific target DNA sequence in the presence of a vast excess of other DNA sequence information. Since the first description in 1989 (Backman and Wang, 1989, European Patent Application No. 0 320 308; Royer et al., 1989, European Patent Application No. 0 324 616; Wallace, 1989, European Patent Application No. 0 336 731; Wu and Wallace, 1989, Genomics 4:560–569; Orgel, 1989; Richards and Jones, 1989) LCR has been improved by the employment of a thermostable DNA ligase in conjunction with non-radioactive detection (Bond et al., 1990).

TABLE 8

Regression on the number of copies of the Pit-1 A allele (gene substitution effect) and on the presence of AB (dominance effect) observed for 455 valid records (lactation length 250–730 days) of 174 Cana cows.

| Trait | Effect | Regression coefficient | SE | Pr > \|T\| |
|---|---|---|---|---|
| Milk yield | A allele | 128 | 333 | 0.70 |
|  | Dominance (AB) | −136 | 378 | 0.72 |
| Fat yield | A allele | 1.40 | 14.27 | 0.92 |
|  | Dominance (AB) | −1.03 | 16.19 | 0.95 |
| Protein yield | A allele | 4.66 | 10.33 | 0.65 |
|  | Dominance (AB) | −5.74 | 11.72 | 0.62 |

2) FLP at the Pit-1 gene using HinfI restriction enzyme was revealed by PCR analysis adapted from Woolard et al., supra.

Using the method described by Sanger et al., supra, we have identified the point mutation at the nucleotide 1178 (a versus g) associated to the reported RFLP. Also, a new PCR method without HinfI restriction enzyme and using primers that overlap the mutation has been developed.

Polymerase Chain Reaction Method

Figure 3:
FIG. 3 is an electrophoretic pattern illustrating the PCR amplification products obtained after amplification with following primers.

The RFLP at the Pit-1 gene was revealed by the polymerase chain reaction (PCR). Briefly, two PCR primers that overlap the mutation (primer AA=5'-CAGAGAG-AAAAACGGGTGAAGACAAGCATA-3' (SEQ ID No:4) and primer BB=5'-CAGAGAGAAAAACGGGTGAAG-ACAAGCATG-3') (SEQ ID No:5) were used in association with a third primer (primer B=5'-GACAGGGAAAG-TGATATAGAAAGGGAGATAGA-3') (SEQ ID No:3) to amplify a 360-bp fragment form the genomic DNA in a 50-µl reaction volumes containing 2 mM MgCl$_2$. Conditions were 95° C. for 3 min, followed by 35 cycles of 95° C. for 1 min, 65.2° C. for 1 min, and 72° C. for 1 min. The final step was 72° C. for 10 min. The PCR products were electrophoresed on 2% agarose gels with 1 µg/ml of ethidium bromide (FIG. 3).

CONCLUSIONS

Two alleles were distinguished for the Pit-1 gene, the growth hormone factor-1/pituitary-specific transcription factor responsible for the activation of prolactin and GH gene expression, using a restriction site recognized by HinfI. Two allele were observed, A not digested and B showing this site. The AA pattern was less frequent than the AB or BB pattern. The significant superiority of the Pit-1 AB pattern or the AA pattern over BB was observed for milk, protein and angularity. This indicates that the heterozygote animals have higher productions and greater dairyness. The fat percentage was found to be lower for AB than for BB animals, a result that results from higher milk by near constant fat yield.

These results show a single action of Pit-1. But, by using a canonical transformation approach it was observed that at least two different actions of Pit-1; one on yields and angularity and another only on angularity. These results can be explain that Pit-1 has more than one role through the activation of prolactin and the GH gene expression. A first role is influencing milk, protein (and fat) yields, a second role is linked to the muscular development of the animals, meaning the presence of AB reducing the muscularity through an improvement of angularity.

Interesting enough, these findings show the usefulness of the canonical transformation to distinguish between effects on related traits. The association of Pit-1 polymorphism and milk traits in dairy cattle was shown on the original, but also on a transformed scale. Relationships were less important for conformation traits, except angularity, a trait that is related to milk yield. Again canonical transformation showed that effects on angularity were only partially a direct consequence of influence of Pit-1 on milk traits.

Identification of a specific mutation in the Pit-1 gene further allows the rapid and sensitive method to be carried out to distinguish between the various alleles and corresponding traits.

SEQUENCE LISTING

<160> NUMBER OF SEQ ID NOS: 7

<210> SEQ ID NO 1
<211> LENGTH: 20
<212> TYPE: DNA
<213> ORGANISM: Unknown
<220> FEATURE:
<223> OTHER INFORMATION: Description of Unknown Organism:Bovine Pit-1
      cDNA

<400> SEQUENCE: 1
aaaccatcat ctcccttctt                                                    20

<210> SEQ ID NO 2
<211> LENGTH: 22
<212> TYPE: DNA
<213> ORGANISM: Unknown
<220> FEATURE:
<223> OTHER INFORMATION: Description of Unknown Organism:Bovine Pit-1
      cDNA

<400> SEQUENCE: 2
aatgtacaat gtgccttctg ag                                                 22

<210> SEQ ID NO 3
<211> LENGTH: 32
<212> TYPE: DNA
<213> ORGANISM: Unknown
<220> FEATURE:
<223> OTHER INFORMATION: Description of Unknown Organism:Primers Pit-B

<400> SEQUENCE: 3
gacagggaaa gtgatataga aagggagata ga                                      32

<210> SEQ ID NO 4
<211> LENGTH: 30
<212> TYPE: DNA
<213> ORGANISM: Unknown
<220> FEATURE:
<223> OTHER INFORMATION: Description of Unknown Organism:Primers Pit-1
      AA

<400> SEQUENCE: 4
cagagagaaa aacgggtgaa gacaagcata                                         30

<210> SEQ ID NO 5
<211> LENGTH: 30
<212> TYPE: DNA
<213> ORGANISM: Unknown
<220> FEATURE:
<223> OTHER INFORMATION: Description of Unknown Organism:Primers Pit-1
      BB

<400> SEQUENCE: 5
cagagagaaa aacgggtgaa gacaagcatg                                         30

<210> SEQ ID NO 6
<211> LENGTH: 276
<212> TYPE: PRT
<213> ORGANISM: Unknown
<220> FEATURE:
<223> OTHER INFORMATION: Description of Unknown Organism:Peptide

<400> SEQUENCE: 6

Met Ser Cys Gln Pro Phe Thr Ser Thr Asp Thr Phe Ile Pro Leu Asn

```
              1               5              10              15
        Ser Glu Ser Ser Ala Thr Leu Pro Leu Ile Met His Pro Ser Ala Ala
                         20              25              30

Glu Cys Leu Pro Val Ser Asn His Ala Thr Asn Val Met Ser Thr Ala
                 35              40              45

Thr Gly Leu His Tyr Ser Val Pro Phe Cys His Tyr Gly Asn Gln Ser
                 50              55              60

Ser Thr Tyr Gly Val Met Ala Gly Ser Leu Thr Pro Cys Leu Tyr Lys
         65              70              75              80

Phe Pro Asp His Thr Leu Ser His Gly Phe Pro Pro Met His Gln Pro
                         85              90              95

Leu Leu Ser Glu Asp Pro Thr Ala Ala Asp Phe Lys Gln Glu Leu Arg
                        100             105             110

Arg Lys Ser Lys Leu Val Glu Glu Pro Ile Asp Met Asp Ser Pro Glu
                    115             120             125

Ile Arg Glu Leu Glu Lys Phe Ala Asn Glu Phe Lys Val Arg Arg Ile
                    130             135             140

Lys Leu Gly Tyr Thr Gln Thr Asn Val Gly Glu Ala Leu Ala Ala Val
        145             150             155             160

His Gly Ser Glu Phe Ser Gln Thr Thr Ile Cys Arg Phe Glu Asn Leu
                        165             170             175

Gln Leu Ser Phe Lys Asn Ala Cys Lys Leu Lys Ala Ile Leu Ser Lys
                        180             185             190

Trp Leu Glu Glu Ala Glu Gln Val Gly Ala Leu Tyr Asn Glu Lys Val
                    195             200             205

Gly Ala Asn Glu Arg Lys Arg Lys Arg Thr Thr Ile Ser Ile Ala
        210             215             220

Ala Lys Asp Ala Leu Glu Arg His Phe Gly Glu Gln Asn Lys Pro Ser
        225             230             235             240

Ser Gln Glu Ile Leu Arg Met Ala Glu Glu Leu Asn Leu Glu Lys Glu
                        245             250             255

Val Val Arg Val Trp Phe Cys Asn Arg Arg Gln Arg Glu Lys Arg Val
                    260             265             270

Lys Thr Ser Leu
                    275

<210> SEQ ID NO 7
<211> LENGTH: 1502
<212> TYPE: DNA
<213> ORGANISM: Unknown
<220> FEATURE:
<223> OTHER INFORMATION: Description of Unknown Organism:DNA
<220> FEATURE:
<221> NAME/KEY: unsure
<222> LOCATION: (1308)..(1310)
<223> OTHER INFORMATION: n at positions 1308-1310 is an unknown
      nucleotide.
<220> FEATURE:
<221> NAME/KEY: unsure
<222> LOCATION: (1334)
<223> OTHER INFORMATION: n at position 1334 is an unknown nucleotide.
<220> FEATURE:
<221> NAME/KEY: unsure
<222> LOCATION: (1391)
<223> OTHER INFORMATION: n at position 1391 is an unknown nucleotide.
<220> FEATURE:
<221> NAME/KEY: unsure
<222> LOCATION: (1406)..(1410)
<223> OTHER INFORMATION: n at positions 1406-1410 is an unknown
      nucleotide.
<220> FEATURE:
```

```
<221> NAME/KEY: unsure
<222> LOCATION: (1414)
<223> OTHER INFORMATION: n at position 1414 is an unknown nucleotide.
<220> FEATURE:
<221> NAME/KEY: unsure
<222> LOCATION: (1421)
<223> OTHER INFORMATION: n at position 1421 is an unknown nucleotide.
<220> FEATURE:
<221> NAME/KEY: unsure
<222> LOCATION: (1495)
<223> OTHER INFORMATION: n at position 1495 is an unknown nucleotide.

<400> SEQUENCE: 7
gcaaatactg tgatttgaag ctaaccaaat aaactaattt ctattttggc tggagaagag      60
aaaggaatga aagtagaaac actcgctatt acacatagga gagcctatct gaattcgaga     120
tgctccttag aaatagtaaa taaactctga ttcaggcttg tcttcacccg tttttctctc     180
tgcttcggtt acaaaaccaa accctcacca cttctttctc caggtttagt tcttcagcca     240
tccgcaggat ctcctgagag aaggcttat tctgttctcc aaagtgtctc tccagggcgt      300
ctttagcagc aatactgatt gttgttctcc gtttctattc ttttgtggga atgagttgcc     360
aaccttttac ttcgactgat acctttatac ctctgaattc tgagtcttct gcaactctgc     420
ctctgataat gcattcccag tgctgcggag tgcctaccgg tctccaacca cgccaccaac     480
gtgatgtcca cagcaacagg acttcaataa tctgttcctt tctgtcatta tggaaaccag     540
tcatcgacct atggcgtgat ggcagggagc ttaacccctt gtctttataa gtttcctgac     600
cacacgttga gtcatggttt tcctcccatg catcagcctc tcctttcaga ggaccccact     660
gccgctgatt tcaagcagga gctcaggcgg aaaagcaaat tggttgaaga gccaatagac     720
atggattctc cagaaatccg agaacttgaa agtttgcca atgagtttaa agtgagaaga      780
attaagctag gatacaccca gacaaatgtt ggggaagctc tggcagctgt gcatggctct     840
gaattcagtc aaacaactat ctgccgattt gaaaacctgc agctcagctt caaaaatgca     900
tgcaaactaa aagcaatatt atccaaatgg ctggaggagg ccgagcaagt aggagcttta     960
tacaatgaga agttggtgc aaatgaaaga aaaggaaac ggagaacaac aatcagtatt      1020
gctgctaaga cgcgctggag agacactttg gagaacagaa taagccttcc tctcaggaga     1080
tcctgcggat ggctgaagaa ctaaacctgg agaaagaagt ggtgagggtt tggttttgta     1140
accgaaggca gagagaaaaa cgggtgaaga caagcctaaa tcagagttta tttactattt     1200
ctaaggagca tctcgaatgc agataggctc tcctattgtg taatagcgat tctactttttc    1260 attcctttct cttctcagcc aaaatagaaa ttagttattt ggttagcnnn aaaaatcaca     1320
tcagtaattt ttgncagaag tgtttctttt ctactttaaa aataaataca atttaaatta     1380
tgttgatgaa ntattctcag aaggannnnn tcantgtaca ntttaagcca aagactaata     1440
ggattaaaac aatgattctg tccctttcac tatatctttc cctctatctc tcccnggaat     1500
tc                                                                   1502
```

What we claim is:

1. A method for distinguishing bovines that are more likely to be superior milk producers from bovines that are more likely to be superior meat producers, compared to one another, said method comprising the steps of:
   detecting a polymorphism in the Pit-1 gene at nucleotide position 1178 of the SEQ ID No: 7 using primer(s) which overlap(s) the mutation in said Pit-1 gene; and analyzing said polymorphism, wherein a AB or AA pattern is associated with superior milk producing capabilities and a BB pattern is associated with superior meat producing capabilities in said bovine, wherein allele A has an adenine at nucleotide position 1178 and allele B has a guanine at the same position.

2. The method of claim 1, wherein the primers overlapping the mutation in the Pit-1 gene are the following:
   ca gagagaaaaa cgggtgaaga caagcat a (Pit-1 AA) (SEQ ID No: 4) for the AA genotype, characteristic of superior milk producing capabilities, and ca gagagaaaaa cgggtgaaga caagcat g (Pit-1 BB) (SEQ ID No: 5) for the BB genotype, characteristic of superior meat producing capabilities.

3. The method of claim 2, wherein a reverse primer used to perform a PCR amplification is the following:

gac agggaaagtg ggagataga (Pit-1 B) (SEQ ID No: 3).

4. A method for distinguishing bovines that are more likely to be superior milk producers from bovines that are more likely to be superior meat producers, compared to one another, said method comprising the steps of:

(1) isolating genomic DNA from a bovine;

(2) detecting a polymorphism in the Pit-1 gene at nucleotide position 1178 of the sequence of SEQ ID No: 7 using primer(s) which overlap(s) the mutation in said Pit-1 gene; and (3) analyzing said polymorphism, wherein a AB or AA pattern is associated with superior milk producing capabilities and a BB pattern is associated with superior meat producing capabilities in said bovine, wherein allele A has an adenine at nucleotide position 1178 and allele B has a guanine at the same position.

5. The method of claim 4, wherein the primers overlapping the mutation in the Pit-1 gene are the following:

ca gagagaaaaa cgggtgaaga caacat a (Pit-1 AA) (SEQ ID No: 4) for the AA genotype, characteristic of superior milk producing capabilities, and ca gagagaaaaa cgggtgaaga caagcat g (Pit-1 BB) (SEQ ID No: 5) for the BB genotype, characteristic of superior meat producing capabilities.

6. The method of claim 5, wherein a reverse primer used to perform a PCR amplification is the following:

gac agggaaagtg atatagaaag ggagataga (Pit-1 B) (SEQ ID No: 3).

7. The method of claim 1, further comprising between steps (1) and (2) the step of:

isolating a fragment from said genomic DNA comprising a fragment of the Pit-1 gene.

* * * * *

UNITED STATES PATENT AND TRADEMARK OFFICE
CERTIFICATE OF CORRECTION

PATENT NO. : 6,492,142 B2  Page 1 of 1
DATED : December 10, 2002
INVENTOR(S) : Robert Renaville et al.

It is certified that error appears in the above-identified patent and that said Letters Patent is hereby corrected as shown below:

Column 25,
Line 6, change "gac agggaaagtg ggagataga" to -- gac agggaaagtg atatagaaag ggagataga --;

Column 26,
Line 15, change "1" to -- 4 --.

Signed and Sealed this

Twelfth Day of August, 2003

JAMES E. ROGAN
*Director of the United States Patent and Trademark Office*